US006183785B1

(12) United States Patent
Westfall

(10) Patent No.: US 6,183,785 B1
(45) Date of Patent: Feb. 6, 2001

(54) TEAT DISINFECTANT

(76) Inventor: Geoffrey J. Westfall, 80 Robbins Rd., Brooklyn, CT (US) 06234

( * ) Notice: Under 35 U.S.C. 154(b), the term of this patent shall be extended for 0 days.

(21) Appl. No.: 09/191,207

(22) Filed: Nov. 12, 1998

(51) Int. Cl.$^7$ .......................... A01N 37/04; A01N 37/52; A01N 55/02; A01N 59/16; A61K 31/155; A61K 31/315; A61K 33/30

(52) U.S. Cl. .......................... 424/642; 424/641; 424/438; 514/494; 514/557; 514/635

(58) Field of Search .................................. 424/641, 642, 424/438, 43; 514/494, 557, 635

(56) References Cited

U.S. PATENT DOCUMENTS

| | | | |
|---|---|---|---|
| 4,049,830 | 9/1977 | Pugliese | 514/727 |
| 4,100,269 | 7/1978 | Pader | 424/49 |
| 4,401,666 | * 8/1983 | Wedig et al. | 514/188 |
| 4,434,181 | 2/1984 | Marks, Sr. et al. | 514/635 |
| 4,548,807 | 10/1985 | Westfall et al. | 424/45 |
| 4,716,032 | 12/1987 | Westfall et al. | 424/45 |
| 5,017,369 | 5/1991 | Marhevka | 514/494 |
| 5,063,249 | 11/1991 | Andrews | 514/673 |
| 5,296,464 | * 3/1994 | Tomita et al. | 514/6 |
| 5,308,868 | 5/1994 | Kefford | 514/560 |
| 5,503,838 | 4/1996 | Schmidt et al. | 424/667 |
| 5,534,266 | 7/1996 | Ricketts | 424/672 |
| 5,618,841 | 4/1997 | Kross | 514/557 |
| 5,641,498 | 6/1997 | Loosemore | 424/405 |
| 5,708,023 | 1/1998 | Modak et al. | 424/407 |
| 5,720,984 | 2/1998 | Ricketts | 424/672 |

OTHER PUBLICATIONS

Block, Seymour S., Disinfection, Sterilization, and Preservation, 4$^{th}$ ed., Lea & Febiger, Philadelphia, pp. 1000–1001, 1991.*

Atherton, D. et al., "E. Zinc and Herpes Simplex", *Pharmacology of the Skin II: Methods Absorption, Metabolism and Toxicity Drugs and Diseases*, 556–557 (Date Unknown).

Brochure, "What you Should Know About . . . Mastitis in Dairy Cows", American Veterinary Medical Association, Schaumburg, Illinois (Date Unknown).

Brochure, "Fight Bac Teat Disinfectant for the Control of Mastitis", Deep Valley Farm, Inc., Brooklyn, Connecticut (Date Unknown).

Brochure, "Prove to Yourself What the Research Shows: You make more with Zinpro®", Zinpro Corporation, 2 pages (Date Unknown).

Brody, I., "Topical Treatment of Recurrent Herpes Simplex and Post–Herpetic Erythema Multiforme with low Concentrations of Zinc Sulphate Solution", *British Journal of Dermatology*, 104:191–194 (1981).

"Dairy Zine with articles for the Dairy Industry professional", http://www.moomilk.com/dairybiz/index.html, 5 pages (Oct. 15, 1998).

Eby, G. et al., "Use of Topical Zinc to Prevent Recurrent Herpes Simplex Infection: Review of Literature and Suggested Protocols", *Medical Hypotheses*, 17:157–164 (1985).

Gavitt, B., "Revolutionary Product Helping Dairy Farmers", *Business Norwich Bulletin*, 1 page (Oct. 26, 1995).

Gertzen, I., "Vet Relaunches Cattle Disinfectant", *Business Norwich Bulletin*, 1 page (Oct. 26, 1995).

Giertsen, E., "Dose–Related Effects of $ZnC_2$ on Dental Plaque Formation and Plaque Acidogenicity in vivo", *Caries Res*, 23:272–277 (1989).

National Mastitis Council, "Current Concepts of Bovine Mastitis", 4th Edition, 40–41, Madison, Wisconsin (1996).

National Mastitis Council Annueal Meeting Proceedings, "Summary of Peer–Reviewed Publications on Efficacy of Premilking and Postmilking Teat Disinfectants Published Since 1980", 276–284 (1997).

Pader, Oral Hygiene Products & Practices, 352, Chapter 10 (Date Unknown).

The Pharmacological Basis of Therapeutics, A Textbook of Pharmacology, Toxicology, and Therapeutics for Physicians and Medical Students, 4th Edition, Chapter 50, 1050–1051 (Date Unknown).

Sunzel, B. et al., "The Effect of Zinc on Bacterial Phagocytosis, Killing and Cytoprotection in Human Polymorphonuclear Leucocytes", *AP MIS*, 103:635–644 (1995).

* cited by examiner

Primary Examiner—John Pak
(74) Attorney, Agent, or Firm—Merchant & Gould P.C.

(57) ABSTRACT

Compositions, systems, and methods for the prevention of mastitis in milk producing animals is provided. In particular, the compositions comprise a source of zinc, preferably zinc gluconate, and chlorhexidine. The composition is applied to the teat of a milk producing animal such as a cow either by dipping the teat therein or spraying the composition thereon.

13 Claims, No Drawings

TEAT DISINFECTANT

FIELD OF THE INVENTION

The present invention is directed to the treatment or prevention of mastitis in milk producing animals. Specifically, the invention provides teat dip compositions and methods for application.

BACKGROUND OF THE INVENTION

As a result of traditional selective breeding methods, milk production in dairy cows far exceeds the requirements of the newborn calf. Because of udder size, position, and anatomic configuration for rapid removal of large volumes of milk, the mammary glands of dairy cows are especially prone to injury and infection. In particular, mastitis, an infection of the mammary gland, is common in milking dairy cows.

Clinically, mastitis typically produces heat, swelling, tenderness and possible deformation of the udder. Although the milk from a mastitic udder is generally safe for human consumption, a major concern is the cost to producers. Mastitis causes a decrease in the amount and quality of milk produced by the infected cow. With decreased quality, the price obtained for the milk likewise decreases. Certain organisms associated with some mastitis can lead to a cow's death, e.g., *Escherichia coli*.

Mastitis is typically caused by bacteria, such as *Streptococcus agalactiae* and *Staphylococcus aureus* which enter the teat through the teat orifice. These bacteria account for about 90 percent of all udder infections.

Typically after milking, a drop of milk remains on the tip of the teat, which can serve as a nidus for bacterial growth. Also, the teat canal is relaxed or dilated from the vacuum applied by the milking machine. The bacteria can then migrate through the teat orifice and into the internal teat cistern to cause inflammation and blockages.

The mastitis causing bacteria can be spread among cows by contaminated milking units or machines, by cow to cow contact, or can be transferred by milking personnel having contaminated hands. General housing conditions, such as stall size, ventilation, bedding material, and access to pasture are also known to have an impact on mastitis spread.

Systemic and local antibiotic administration is a proven method of mastitis treatment and prevention. Intramammary administration of antibiotics during non-lactating periods, known as dry cow therapy, is an established method for mastitis prevention when a cow is not lactating. For cows that are lactating, teat dips have long been used as a preventative for mastitis. Post milking teat dipping is considered to be the single most important factor in mastitis prevention. Teat dips can function by providing a physical barrier to bacterial entry through the teat orifice. Additionally, bacteria that may be present can be killed by antibacterial ingredients of some teat dips. Typically, the procedure of applying teat dip includes filling a cup or other suitable container with the dip formulation and dipping the teat therein. An aerosol spray generally may include the same or a slightly modified composition of the liquid dip and is sprayed on to the teat. The aerosol spray generally functions in the same manner as dips, with the exception that the aerosol can have a chilling effect on the teat, causing the sphincter muscle and teat orifice to contract, providing a further obstacle to prevent bacterial entry. Sometimes, a teat dip is applied with a pump sprayer.

Known active ingredients for teat dips include chlorine, iodine, in particular an iodophor, and chlorhexidine acetate and chlorhexidine gluconate. Some dip formulations have been developed which combine the desired germicidal or antibacterial properties of the active ingredients with suitable softeners or emollients, such as glycerin.

Although these well known and commercially available teat dips do have a beneficial effect on preventing the spread of mastitis there is a continuing need for improved compositions and systems for treating and preventing mastitis.

SUMMARY OF THE INVENTION

The present invention relates to new and improved compositions, systems, and methods for the prevention of mastitis. In another aspect, the present invention relates to a new and improved composition for the reduction of the spread of mastitis.

In one embodiment, the present invention relates to new compositions for application to the teat orifice of a cow for preventing and treatment of mastitis. In one embodiment, the compositions can comprise a combination of chlorhexidine and zinc. Typically, the chlorhexidine is present in the composition at a weight percent of about 0.1% to 4%. In a preferred embodiment, the chlorhexidine is present at a weight percent of about 0.5%. In one embodiment, zinc gluconate is typically present in the composition at a weight percent of about 0.01% to 5%. Other zinc compounds may be used at a level to provide a similar disassociated zinc ion concentration. In a preferred embodiment, zinc gluconate is present at a weight percent at least about 0.5%, typically greater than about 1%, and preferably present at an amount of about 1.0%–1.5%, for example, 1.25%.

In another embodiment, a system for preventing mastitis is presented. The system comprises a composition including a combination of chlorhexidine and zinc and a container for containing the composition therein. The container can be a cup, jar or similar container, or can be a vessel from which the composition can be sprayed.

In yet another embodiment, a containerized product for use in preventing mastitis is presented. A container capable of being pressurized has a disinfectant composition therein, the composition comprising chlorhexidine and zinc. Preferably, the composition is water based and comprises about 0.1% to 4% chlorhexidine, 0.01% to 5% zinc, and an aerosol propellant.

A method for preventing mastitis comprises the steps of preparing a composition comprising a combination of chlorhexidine and zinc, and applying the composition to the teat of a mammal, such as a cow.

The composition can be applied to the teats of a cow by dipping the teats therein. Alternatively, the composition can be sprayed on to the teats, for example, as an aerosol.

DETAILED DESCRIPTION OF THE PREFERRED EMBODIMENT

Before the present composition and methods of use are disclosed and described, it is to be understood that this invention is not limited to the particular examples, compositions or methods disclosed herein, and that materials and methods may vary somewhat. It is also to be understood that the terminology used herein is used for the purpose of describing particular embodiments only and is not intended to be limiting.

The compositions and methods of the present invention are suitable for use with any milk producing mammals including, for example, cattle, sheep, goats, llamas, pigs, etc. Because cattle are one of the most common milk producing animals, the present invention is described with reference to dairy cattle. However, the invention should not be construed as being limited to cattle.

A single lactating dairy cow is capable of producing about 4 to 13 gallons of milk per day. Cows are typically milked at least twice per day to maintain health and milk production. During milking, milk from the udder flows into individual teats. In the teat the milk flows into the teat cistern and then into the teat orifice, where it passes from the teat in a flow controlled by the teat sphincter muscle. Modem milking systems apply a pulsatile vacuum to the teat so that the sphincter muscle is intermittently opened and closed to release the milk. To keep the cows healthy and to maintain good milk production, it is beneficial to take steps to prevent the onset of mastitis. One common preventative is application of a teat dip composition to the teats after milking.

The present invention provides teat dip compositions and methods for application which maintain hygiene and help prevent mammary infections. The compositions of the invention are typically applied to the skin of the teat, in particular to skin surrounding the teat orifice, as either a liquid (teat dip) or a spray, for example, an aerosol or pump. The composition of the present invention includes a zinc compound, an antibiotic, antibacterial or other disinfectant component, and optional ingredients such as emollients, diluents, and dyes.

The zinc compound can be in a salt form, for example, zinc gluconate, zinc acetate, zinc acetate dihydrate, zinc citrate, zinc sulfate, zinc oxide, zinc chloride, zinc fluoride, zinc nitrate, etc. A zinc composition such as zinc bacitracin may also be useful. Typically, if zinc gluconate is used, the zinc compound is present in a range of about 0.01% to 5% by weight of the total teat dip composition, preferably 0.05% to 4%, more preferably about 0.25% to 1.5%, and most preferably about 1.0% to 1.5%. An example of particularly preferred level of zinc gluconate is about 1.25%. When other zinc compounds are used, the weight percent of these other zinc compounds should be selected so as to provide a similar amount of disassociated zinc ions as that provided by the zinc gluconate in the compositions disclosed herein.

Throughout the specification, the term "disinfectant component" is used to generically refer to an antibiotic, antibacterial or other antimicrobial agent. Preferably, the disinfectant compound is chlorhexidine or a salt thereof. Examples of usable salts include chlorhexidine gluconate, chlorhexidine acetate or diacetate. Other disinfectants such as iodine (preferably povidone iodine) or quaternary ammonium could also be used. Preferably, the disinfectant is present in a range of about 0.1% to 4% by weight of the total teat dip composition, most preferably about 0.5%. The zinc and disinfectant are typically present in the composition at a ratio of about 1:2 to 4:1 zinc:disinfectant, preferably about 2 or 3:1.

In some formulations a lubricant or emollient can be added, preferably in a range of about 0.5% to 20%. Suitable lubricants and emollients are well known and can be used for either dips or spray compositions. Water soluble emollients, such as glycerin (a.k.a. glycerine), glycerol, sorbitol or water-dispersible lanolin, are preferred. Glycerin, at a level of about 10% by weight of the total composition, is preferred.

Generally, the majority of the composition, or "carrier", is a liquid. The carrier may or may not act as a solvent for solubilizing the active ingredients of the composition (that is, the zinc and disinfectant). Usable liquid carriers include water (including tap water, distilled water, deionized water), and alcohol, preferably the lower alkanols of 3 carbon atoms or less, such as propanol, ethyl alcohol and methyl alcohol. The carrier is generally the largest portion of the formulation, typically present in a range of about 40% to 98% by weight, preferably about 70%. Alcohol, if present, is typically in a range up to about 70%; a preferred level for ethyl alcohol is about 10%.

The composition may also include additional additives, such as pigment or dye, to act as an indicator whether a particular cow has been treated with the composition. Typically, a dye, for example FD & C Blue Dye #3, is included in a range of about 0.01% to 1.0%, preferably about 0.05% of the total composition.

The composition can be applied to the teat either as a "dip", directly from a cup or similar container, or can be applied as a spray. If it is desired that the composition is applied as an aerosol spray, a propellant such as dimethyl ether, which can also function as a carrier, can be included. The propellant component, which is preferably water or alcohol soluble, may be present in a range of about 10% to 50%, preferably about 30%. Additional information regarding incorporating the composition into an aerosol can be found in U.S. Pat. Nos. 4,548,807 and 4,716,032 both to Westfall et al., both incorporated herein by reference. A composition of the present invention can also be applied by non-aerosol spray methods such as trigger or pump sprays.

Other components and additives may be optionally added, for example, stabilizers, and suitable corrosion inhibitors, which are particularly desirable when a tin plate container is used to dispense the composition.

The composition of the present invention may be prepared by mixing all the components, except the propellant if used. If propellant is used, the mixture is poured in to a suitable container to be pressurized, after which the propellant is added under suitable pressurized conditions in accordance with conventional methods which are known. A container capable of being pressurized typically has a valve including an orifice nozzle discharge device capable of directing the disinfectant composition outwardly from the container.

In use, a composition of the invention will typically be applied to the teat immediately after milking.

The invention will be further described and illustrated in the examples which follow. The examples are illustrative of the invention and should not be construed as limiting the scope to their details. All parts, percentages, ratios, etc. are by weight unless otherwise specified.

EXAMPLES

A base mixture was prepared by mixing 0.5 part chlorhexidine gluconate, 10 parts glycerin, 70 parts distilled water, 0.05 part FD & C Blue Dye #3, and 10 parts ethyl alcohol. This composition is commercially available under the trade designation "FIGHT BAC® Teat Disinfectant for the Control of Mastitis".

Example 1 was prepared by adding zinc gluconate to the base mixture to provide a level of 0.25% zinc gluconate.

Example 2 was prepared by adding zinc gluconate to the base mixture to provide a level of 0.5% zinc gluconate.

Example 3 was prepared by adding zinc gluconate to the base mixture to provide a level of 1.0% zinc gluconate.

Example 4 was prepared by adding zinc gluconate to the base mixture to provide a level of 1.5% zinc gluconate.

Each mixture prepared above was divided approximately in half; one half was placed in a jar and stored, and the other half was mixed with dimethyl ether (an aerosol propellant)

and pressurized to provide a sprayable mixture with about 30% propellant in a can.

A sample of each Example composition was mixed with milk to provide a solution of 75% Example mixture and 25% milk. Bacterial solutions of *E. coli*, *Staphylococci aureus*, and *Streptococci agalactiae*, each $10^8$ bacteria/ml, were provided.

0.1 ml of each bacterial solution was added to 0.1 ml of the Example composition/milk solution. These solution were thoroughly mixed before being applied to the surface of a blood agar plate. After a set time period, either 5 seconds, 5 minutes or 15 minutes, the combined solutions were streaked across the agar plate. After 18 hours of incubation, the number of resulting colonies on the agar were counted. The results are reported in Tables 1–5.

TABLE 1

Example composition from jars; tested on *Staphylococci aureus*

| | Time | | |
|---|---|---|---|
| Example | 5 seconds | 5 minutes | 15 minutes |
| Base Mixture | ~1000 | 66 | 48 |
| 1 | ~1000 | 6 | 2 |
| 2 | ~1000 | 0 | 0 |

TABLE 2

Example composition from spray can; tested on *Staphylococci aureus*

| | Time | | |
|---|---|---|---|
| Example | 5 seconds | 5 minutes | 15 minutes |
| Base Mixture | ~1000 | ~200 | ~500 |
| 1 | ~500 | 60 | 48 |
| 2 | ~500 | 76 | 16 |

TABLE 3

Example composition from jars; tested on *E. coli*

| | Time | | |
|---|---|---|---|
| Example | 5 seconds | 5 minutes | 15 minutes |
| Base Mixture | ~3000 | ~3000 | ~2000 |
| 1 | ~3000 | ~1000 | ~1000 |
| 2 | ~3000 | 102 | 90 |

TABLE 4

Example composition from spray can; tested on *E. coli*

| | Time | | |
|---|---|---|---|
| Example | 5 seconds | 5 minutes | 15 minutes |
| Base Mixture | ~3000 | ~500 | ~200 |
| 1 | ~3000 | ~200 | ~200 |
| 2 | 79 | 47 | 50 |

TABLE 5

Example composition from spray can; tested on *Streptococci agalactiae*

| | Time | | |
|---|---|---|---|
| Example | 5 seconds | 5 minutes | 15 minutes |
| Base Mixture | 40 | 0 | 0 |
| 1 | 41 | 0 | 0 |
| 2 | 2 | 0 | 0 |

The results from above show that addition of zinc to the teat dip decreased the bacteria counts when compared to only chlorhexidine.

From the foregoing detailed description and examples, it will be evident that modifications and variations can be made in the products and processes of the invention without departing from the spirit or scope of the invention. Therefore, it is intended that all modifications and verifications not departing from the spirit of the invention come within the scope of the claims and their equivalents.

I claim:

1. A method for treating a mammalian teat, the method comprising: applying a hygiene maintaining composition to the teat of a mammal wherein the composition comprises a combination of chlorhexidine and zinc, the zinc provided in a salt form selected from the group consisting of zinc gluconate, zinc acetate, zinc acetate dihydrate, zinc citrate, zinc sulfate, zinc oxide, zinc chloride, zinc fluoride and zinc nitrate.

2. The method according to claim 1 wherein the step of applying the hygiene maintaining composition is by dipping the teat into the composition.

3. The method according to claim 1 wherein the step of applying the hygiene maintaining composition is by spraying the composition on the teat.

4. The method according to claim 3 wherein the hygiene maintaining composition is sprayed on the teat using an aerosol propellant.

5. The method according to claim 1 wherein the zinc salt is present in a range of about 0.01% to 5% by weight of the total hygiene maintaining composition.

6. The method according to claim 5 wherein the zinc salt is zinc gluconate.

7. The method according to claim 1 wherein said chlorhexidine is a chlorhexidine salt.

8. The method according to claim 1 wherein the chlorhexidine is present in a range of about 0.1% to 4% by weight of the total hygiene maintaining composition.

9. The method according to claim 1 wherein the mammal is bovine.

10. A method of reducing bacteria counts associated with milk producing animals, the method comprising:
    selecting a composition comprising chlorhexidine and zinc, the zinc provided in a salt form selected from the group consisting of zinc gluconate, zinc acetate, zinc acetate dihydrate, zinc citrate, zinc sulfate, zinc oxide, zinc chloride, zinc fluoride and zinc nitrate; and
    topically applying the composition to a teat of an animal.

11. The method according to claim 10 wherein the animal is a cow.

12. The method according to claim 10 wherein the step of applying the composition comprises spraying the composition from a container.

13. The method according to claim 10 wherein the step of applying the composition comprises dipping the teat into a container that contains said composition comprising chlorhexidine and zinc.

* * * * *

UNITED STATES PATENT AND TRADEMARK OFFICE
CERTIFICATE OF CORRECTION

PATENT NO. : 6,183,785 B1
DATED : February 6, 2001
INVENTOR(S) : Westfall

It is certified that error appears in the above-identified patent and that said Letters Patent is hereby corrected as shown below:

Title page,
OTHER PUBLICATIONS, column 2, line 23, "Annueal" should read -- Annual --

Column 2,
Line 19, "preventing" should read -- prevention --

Column 5,
Line 15, "solution" should read -- solutions --

Signed and Sealed this

Nineteenth Day of March, 2002

Attest:

JAMES E. ROGAN
Attesting Officer
Director of the United States Patent and Trademark Office